United States Patent [19]

Heltman

[11] Patent Number: 4,682,371
[45] Date of Patent: Jul. 28, 1987

[54] PROTECTIVE EYE PATCH

[76] Inventor: Carolyn R. Heltman, 84 Gallows Hill Rd., West Redding, Conn. 06896

[21] Appl. No.: 916,742

[22] Filed: Oct. 6, 1986

[51] Int. Cl.[4] .......................... A61F 9/00; A61F 13/12
[52] U.S. Cl. ..................................... 2/15; 128/132 R
[58] Field of Search ........................... 2/15; 128/132 R

[56] References Cited

U.S. PATENT DOCUMENTS

| | | | |
|---|---|---|---|
| 2,389,223 | 11/1945 | Werner | 2/15 |
| 2,643,382 | 6/1953 | McLeod | 2/15 |
| 3,068,863 | 12/1962 | Bowman | 128/132 R |
| 3,092,103 | 6/1963 | Mower | 128/132 R |
| 4,599,746 | 7/1986 | Stoner | 2/15 |

Primary Examiner—Louis K. Rimrodt
Attorney, Agent, or Firm—Parmelee, Miller, Welsh & Kratz

[57] ABSTRACT

A socket-shaped, lightweight, substantially rigidly framed, improved eye patch is provided that is to be adhesively, securely mounted on a surrounding bone structure of an eye. It is constructed to conform to the facial structure of a wearer, has hidden adhesive mounting tabs, provides a fabric-enclosing frame and is adaptable to a suitable spaced relation of its fabric covering material with respect to the eye of the wearer.

6 Claims, 7 Drawing Figures

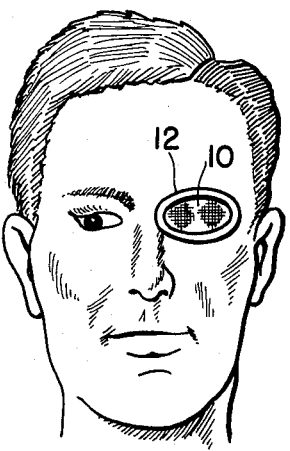
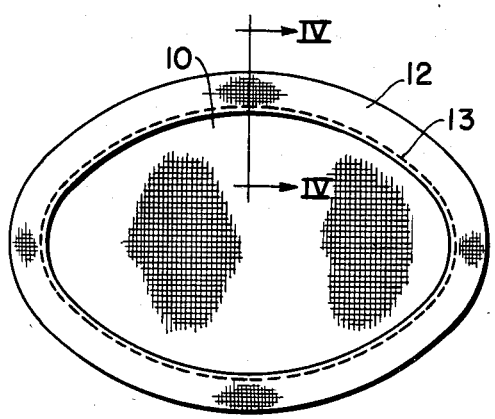
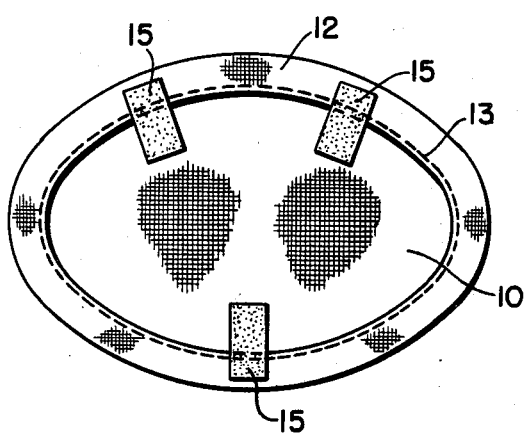
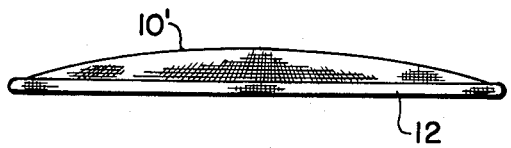
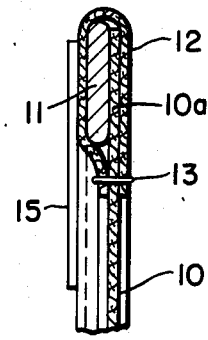
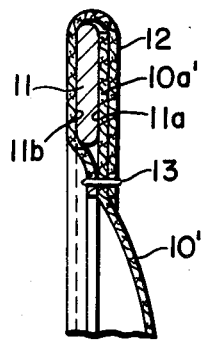
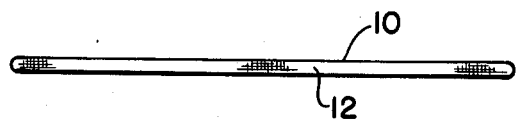

PROTECTIVE EYE PATCH

This invention relates to an orthoptic eye patch device which is improved in appearance, eye mounting relationship and medical adaptability in its construction and utilization.

It has been devised to provide a lightweight, easily mounted and removed eye socket cover device that assures a precise and trim coverage and fit about an eye socket area, and that is primarily for medical usage where, for example, an eye has been damaged, operated on or is to be protected. It eliminates difficulties which have been heretofore encountered in eye patch devices and their utilization.

The device of the present invention has been devised and constructed to provide full protection without unsightliness and to substantially correspond in shape to an eyeglass while, at the same time, enabling a fully protective covering of the eye, to either prevent or permit normal eyelash movement as desired, and to provide a securely mounted positioning on the surrounding bone structure of an eye socket, and without unsightly ties or projecting tabs. As constructed, it enables a normal lid winking relation, if desired, and also if the eyelashes are extremely long and would normally be hindered in their movement.

BRIEF DESCRIPTION OF THE DRAWINGS

In the drawings,

FIG. 1 shows a patch constructed in accordance with the invention in a normal bridging mounted relation over an eye socket of a wearer to give full protection to and cover his eye;

FIG. 2 is an enlarged front plan view of a device of the invention showing its construction;

FIG. 3 is a back plan view of the same scale as FIG. 2 showing adhesive tabs for removably securing the device in a wearing position;

FIG. 4 is an enlarged fragmental sectional view taken along the line IV—IV of FIG. 2 and showing the details of the construction of the device;

FIG. 5 is an edge view on the scale of FIG. 2 showing the construction of FIG. 4 in which the fabric material extends in a planar relation from a front face of a frame therefore;

FIG. 6 is a view taken along the same line as FIG. 4, but illustrating a modified embodiment of the invention in which a central closing-off area of covering fabric material will be provided with a pre-shaped outwardly convex, inwardly concave shape;

And, FIG. 7 is an edge view similar to and on the scale as FIG. 5 but of the modified construction shown in FIG. 6.

DETAILED DESCRIPTION OF THE DRAWINGS

Referring particularly to FIGS. 2, 3 and 4 of the drawings, I have shown an eye patch provided with an enclosing, continuous, outer rim or frame member 11 of substantially rigid but lightweight material, such as of aluminum metal or plastic material. The frame 11 is shown of oval or eye lens-like shape to substantially conform to the shape of a normal eye socket. As shown particularly in FIG. 4, the frame 11 has a pair of opposed, planar front and back, relative wide faces 11a and 11b of planar shape and a pair of connecting, relatively narrow, rounded edges that define a central open portion. An outer border or edge portion 10a of a fabric-like cover material 10 is shown positioned to extend in a planar relation along the front face 11a, and as secured thereon by a lapped-over, continuous piece of relatively soft fabric-like strip material 12 which serves as a protective buffer between the frame 11 and the skin of a wearer. As shown in FIGS. 2 and 4, thread stitching 13 extends through a three thickness of material as represented by enclosing flap ends of the strip material 12 and an enclosed, intermediately positioned edge portion 10a of the cover material 10.

It is important to avoid irritation and fatigue of supporting flesh about the eye and, at the same time, to provide substantial rigidity such that the patch will retain the closing-off fabric material 10 in a relatively tight closing-off relation at all times while it is being worn. As shown in FIG. 4, the outer peripheral edge portion 10a of the fabric cover material 10 is positioned on the front planar face of the frame 11 and is enclosed by the folded-over framing strip of fabric material 12 in such a manner that a back side of the strip 12 extends along and abuts the planar back face of the frame 12, and a front side of the strip abuts the front side of the edge portion 10a. The frame 11 is thus fully enclosed at its end as well as along its opposite planar faces in such a manner that no portion of it is exposed. The stitching 13 is shown extending fully along the continuous extent of the frame 11 and through three layers of fabric material as represented by the enclosing strip material 10 and the edge portion of the framing strip material 12. The covering material 10, as mounted, is shown as having a relatively tight, cross extending, closing-off relation with respect to the central opening or window defined by the frame 11.

To removably secure the device in position about the eye of the wearer, I have provided adhesive tabs 15 in an as shown substantially balanced spaced relation about the frame 11 that have double-sided adhesive thereon. Such an adhesive material is readily available in rolls from adhesive tape manufacturers, such as Minnesota Mining and Manufacturing. As indicated, a pair of tabs 15 are mounted in an above spaced-apart relation to extend substantially diagonally inwardly along the cover material 10, rather than outwardly, such that they are not visible from outside the patch in its mounted relation of FIG. 1. If desired, one or more below-positioned tabs 15 may also be provided. It will be noted that the use of tabs 15 having dual or opposite-sided adhesive thereon enables their ready replacement if and when they loose their adhesiveness or become soiled.

In the modified embodiment of FIGS. 5 and 6, the construction is generally the same, except that the covering material 10 is impregnated with a suitable stiffening material, such as starch or a resin, to give it an outwardly convex, inwardly concave shape. This construction is particularly advantageous under certain conditions, such as where there may be some form of bandage over the eye or the eyelashes of wearer are of unusual length. It will be noted that the mounting of the covering material 10 on the front face 11a of the frame 11 provides additional clearance, as controlled by the thickness of the frame 11.

The construction provides a patch that is trim, neat and pleasing in appearance when applied to the wearer (see FIG. 1); it is comfortable to wear and is easily applied and removed; it is inexpensive to produce, and is fully adaptable and may be proportioned to any and all known eye covering and protecting needs. The patch is designed to conform with the natural contours of the face of the wearer and an eye socket, to minimize and hide its mounting means, to avoid skin irritation due to frame contact, etc. with the skin, to fit within the natural eye socket and on surrounding bone area, and to provide a desired spacing between its closing fabric window, the eyelid, the eye or any eye bandaging, etc.

I claim:

1. An aesthetically and medically improved eye patch of the character shown and described which comprises, an enclosing substantially rigid continuous frame member of lightweight material such as aluminum or plastic, said frame member defining a central opening and having a pair of opposed substantially planar front and back faces and connecting inner and outer edges, fabric-like covering material securely mounted on said frame member and having an inwardly extending portion secured in position on one planar face of said frame member as a sole closing-off means for the central opening, relatively short length adhesive tabs having one adhesive side adapted to be secured in a substantially balanced spaced-apart relation on said covering material to extend substantially diagonally inwardly from the back planar face of said frame along a back face of the covering material, said tabs projecting only inwardly towards the central opening of said frame and having an opposite adhesive side to mount and adhesively secure the patch in alignment with and about surrounding bone structure of a wearer that defines his or her eye socket in such a manner that the frame member will extend in a substantially horizontal shape-conforming relation about the eye socket of the wearer, that the covering material will have and retain a desired relation with respect to the eyelid of the wearer, and that said adhesive tabs will be invisible from the outside of the patch in its mounted relation.

2. An improved eye patch as defined in claim 1 wherein said extending portion of the covering material extends in a planar relation across the central opening.

3. An improved eye patch as defined in claim 1 wherein said extending portion of the covering material is impregnated with stiffening material and extends in an outwardly convex and inwardly concave relation across the central opening.

4. An improved eye patch as defined in claims 2 and 3 wherein, said covering material comprises a strip portion, said extending portion has an edge portion positioned to extend along said planar front face of said frame, and said covering material extend around said frame and laps over said edge portion, and means extending through said covering material and said edge portion to secure them in a tightly secure relation on said frame.

5. An improved eye patch of the character shown and described for mounting about an eye socket of a wearer which comprises, a continuous oval-shaped enclosing substantially rigid outer frame member of lightweight material such as aluminum or plastic, said frame member defining a central open portion substantially conforming to the shape of an eye socket and having a pair of opposed substantially planar front and back faces, a fabric-like covering material closing-off the central open portion and having an edge portion in a planar abutting relation along one of said planar faces of said frame member, a mounting strip of relatively soft fabric-like material enclosing said frame member and the edge portion of said covering material, and stitch means extending through said mounting strip and the edge portion of said covering material to secure said covering material in a substantially tight cross-extending position on said frame member, and adhesive tabs of relatively short length adhesively replaceably secured on one side to said mounting strip in a spaced-apart relation along said frame to project inwardly from said frame towards said covering material, and said tabs having an adhesive opposite side for removably mounting said patch about an eye socket of the wearer.

6. An improved eye patch as defined in claim 5 wherein said adhesive tabs are of a dual adhesive-faced construction, and said edge portion of said covering material extends along the planar front face of said frame member.

* * * * *